(12) United States Patent
Rao et al.

(10) Patent No.: US 11,284,939 B2
(45) Date of Patent: Mar. 29, 2022

(54) IRRIGATED CATHETER WITH IMPROVED ABLATION TIP ELECTRODE FLUID DISTRIBUTION

(71) Applicant: Biosense Webster (Israel) Ltd., Yokneam (IL)

(72) Inventors: Anand R. Rao, Tustin, CA (US); Thanh Nguyen, El Monte, CA (US); Keshava Datta, Chino Hills, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 19 days.

(21) Appl. No.: 15/643,414

(22) Filed: Jul. 6, 2017

(65) Prior Publication Data

US 2019/0008581 A1   Jan. 10, 2019

(51) Int. Cl.
| | |
|---|---|
| *A61B 18/14* | (2006.01) |
| *A61M 25/00* | (2006.01) |
| *A61M 25/01* | (2006.01) |
| *A61B 18/00* | (2006.01) |

(52) U.S. Cl.
CPC ....... *A61B 18/1492* (2013.01); *A61M 25/005* (2013.01); *A61M 25/007* (2013.01); *A61M 25/0045* (2013.01); *A61M 25/0082* (2013.01); *A61M 25/0147* (2013.01); *A61B 2018/00029* (2013.01); *A61B 2018/00357* (2013.01); *A61B 2018/00577* (2013.01); *A61B 2018/00821* (2013.01); *A61B 2218/002* (2013.01); *A61M 25/0136* (2013.01); *A61M 2025/0046* (2013.01)

(58) Field of Classification Search
CPC ...... A61B 18/1492; A61B 2018/00029; A61B 2218/002; A61B 2018/00357; A61B 2018/00577; A61B 2018/00821; A61M 25/007; A61M 2025/0073; A61M 25/0069; A61M 25/0045; A61M 25/005; A61M 25/0082; A61M 25/0147; A61M 25/0136; A61M 2025/0046
See application file for complete search history.

(56) References Cited

U.S. PATENT DOCUMENTS

| | | | |
|---|---|---|---|
| 6,053,912 A * | 4/2000 | Panescu | A61B 18/1492 606/31 |
| 8,357,152 B2 | 1/2013 | Govari et al. | |
| 8,792,962 B2 | 7/2014 | Esguerra et al. | |
| 2003/0216710 A1 * | 11/2003 | Hurt | A61M 25/007 604/523 |
| 2005/0065511 A1 * | 3/2005 | Geistert | A61B 18/1492 606/41 |

(Continued)

OTHER PUBLICATIONS

Extended European Search Report for corresponding European Application No. 18181837.8, dated Oct. 8, 2018, 7 pages.

*Primary Examiner* — Eun Hwa Kim
*Assistant Examiner* — Adam Z Minchella
(74) *Attorney, Agent, or Firm* — Lewis Roca Rothgerber Christie LLP

(57) ABSTRACT

A catheter has a two-piece tip electrode with a shell and a support structure defining a chamber, and a fluid distribution tube that extends longitudinally into the chamber, the fluid tube having fluid apertures along its length for distributing fluid more uniformly distributed throughout the chamber for improved cooling and thus minimizing the risk of char formation on regions of the tip electrode more prone to overheating.

20 Claims, 7 Drawing Sheets

(56) References Cited

U.S. PATENT DOCUMENTS

| | | | |
|---|---|---|---|
| 2005/0070894 A1* | 3/2005 | McClurken | A61B 18/1492 |
| | | | 606/48 |
| 2005/0107738 A1* | 5/2005 | Slater | A61M 25/10 |
| | | | 604/96.01 |
| 2005/0187561 A1* | 8/2005 | Lee-Sepsick | A61B 17/42 |
| | | | 606/108 |
| 2006/0074388 A1* | 4/2006 | Dextradeur | A61L 29/16 |
| | | | 604/265 |
| 2006/0149192 A1* | 7/2006 | Deniega | A61M 25/0043 |
| | | | 604/264 |
| 2007/0156114 A1* | 7/2007 | Worley | A61B 18/1492 |
| | | | 604/525 |
| 2007/0255230 A1* | 11/2007 | Gross | A61B 17/8811 |
| | | | 604/272 |
| 2008/0255540 A1 | 10/2008 | Selkee | |
| 2009/0005768 A1* | 1/2009 | Sharareh | A61B 18/1492 |
| | | | 606/17 |
| 2010/0152731 A1* | 6/2010 | de la Rama | A61M 25/0074 |
| | | | 606/41 |
| 2010/0168827 A1 | 7/2010 | Schultz | |
| 2011/0130648 A1 | 6/2011 | Beeckler et al. | |
| 2011/0270244 A1 | 11/2011 | Clark et al. | |
| 2012/0035605 A1* | 2/2012 | Tegg | A61B 18/1492 |
| | | | 606/41 |
| 2013/0030385 A1* | 1/2013 | Schultz | A61B 18/1492 |
| | | | 604/247 |
| 2014/0200441 A1* | 7/2014 | Potter | A61M 3/0279 |
| | | | 600/424 |
| 2014/0276759 A1* | 9/2014 | Kim | A61B 18/1492 |
| | | | 606/33 |
| 2015/0351832 A1 | 12/2015 | Oliverius et al. | |
| 2016/0184008 A1 | 6/2016 | Papaioannou et al. | |

* cited by examiner

IRRIGATED CATHETER WITH IMPROVED ABLATION TIP ELECTRODE FLUID DISTRIBUTION

FIELD OF INVENTION

The present invention relates to electrophysiologic (EP) catheters, in particular, EP catheters for ablating cardiac tissue.

BACKGROUND

Ablation of cardiac tissue is well known as a treatment for cardiac arrhythmias. In radio-frequency (RF) ablation, for example, a catheter is inserted into the heart and brought into contact with tissue at a target location. RF energy is then applied through electrodes on the catheter to heat tissue to a destructive temperature in order to create a lesion for the purpose of breaking arrhythmogenic current paths in the tissue.

Irrigated catheters are now commonly used in ablation procedures. Irrigation provides many benefits including cooling of the electrode and tissue which prevents overheating of tissue that can otherwise cause adjacent blood to form char and coagulum. Irrigated tip electrodes are known, including tip electrodes with a two-piece construction having an inner support structure and a dome shell mounted thereon. A cavity is formed between the support structure and the dome shell to provide a plenum chamber that enables a flow of fluid exiting the tip electrode via fluid ports formed in the dome shell. However, irrigation fluid may not be uniformly distributed throughout the plenum chamber and thus not all portions of the dome shell may receive uniform cooling. Without uniform cooling, hot spots may result which lead to char formation during ablation.

Accordingly, it is desirable that a catheter with a plenum chamber receive more consistent and evenly distributed irrigation cooling to all portions of the dome shell to minimize char formation. It is desirable for the irrigation to reach proximal end portion of the dome shell and other regions with a lesser number of fluid exit ports in the dome shell.

SUMMARY OF THE INVENTION

A catheter has a tip electrode a shell and a support structure defining a fluid plenum chamber. The catheter advantageously includes a fluid distribution tube that extends longitudinally into the chamber, wherein the fluid distribution tube has fluid apertures along its length for distributing fluid more uniformly throughout the chamber in improved cooling and thus minimizing the risk of char formation on regions of the tip electrode more prone to overheating.

In some embodiments of the present invention, an electrophysiologic catheter has an elongated catheter body, a control handle proximal of the catheter body, and a tip electrode distal of the catheter body, the tip electrode configured for irrigation and having a shell and a support member defining an internal chamber. The tip electrode includes a fluid distribution tube that extends longitudinally into the chamber and has a side wall with a plurality of apertures.

In some detailed embodiments, the apertures in the side wall of the fluid distribution tube are arranged in a predetermined pattern.

In some detailed embodiments, the predetermined pattern includes a distal aperture and a proximal aperture.

In some detailed embodiments, the predetermined pattern includes the plurality of apertures are longitudinally aligned.

In some detailed embodiments, the predetermined pattern includes a greater spacing between more-proximal adjacent apertures and a lesser spacing between more-distal adjacent apertures in the longitudinal direction.

In some detailed embodiments, the apertures have different sizes.

In some detailed embodiments, the apertures have different shapes.

In some detailed embodiments, the predetermined pattern includes the apertures having different radial positions in the side wall.

In some detailed embodiment, the catheter includes an irrigation tubing in fluid communication with the fluid distribution tube.

In some detailed embodiments, the internal chamber has a first length and the fluid distribution tube has a second length that ranges between 0.5 and 0.9 of the first length.

In some detailed embodiments, at least one aperture is more proximal than one or more most-proximal ports.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1:
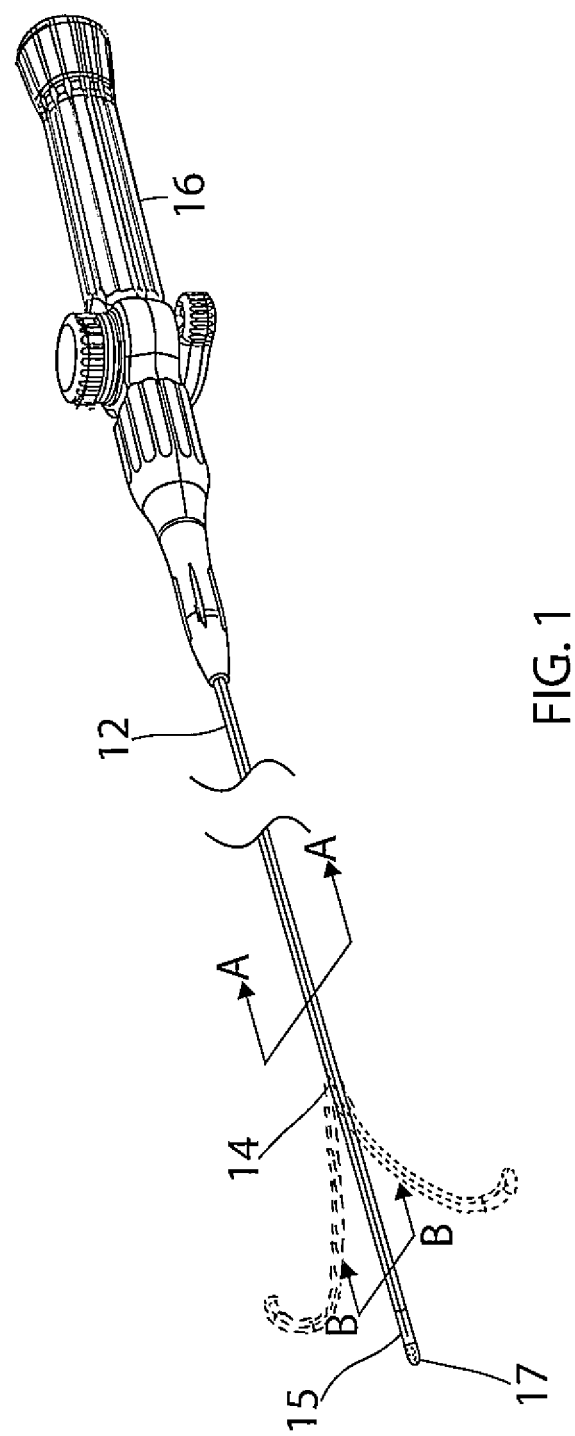
FIG. 1 is a perspective view of catheter in accordance with an embodiment of the present invention.

FIG. 1 illustrates an embodiment of a catheter 10 with an improved irrigation-cooled ablation tip electrode. The catheter has an elongated catheter body 12 with proximal and distal ends, an intermediate deflectable section 14 at the distal end of the catheter body 12, and a distal section 15 with a tip electrode 17. The catheter also includes a control handle 16 at the proximal end of the catheter body 12 for controlling deflection (single or bi-directional) of the intermediate section 14 relative to the catheter body 12.

Figure 2:
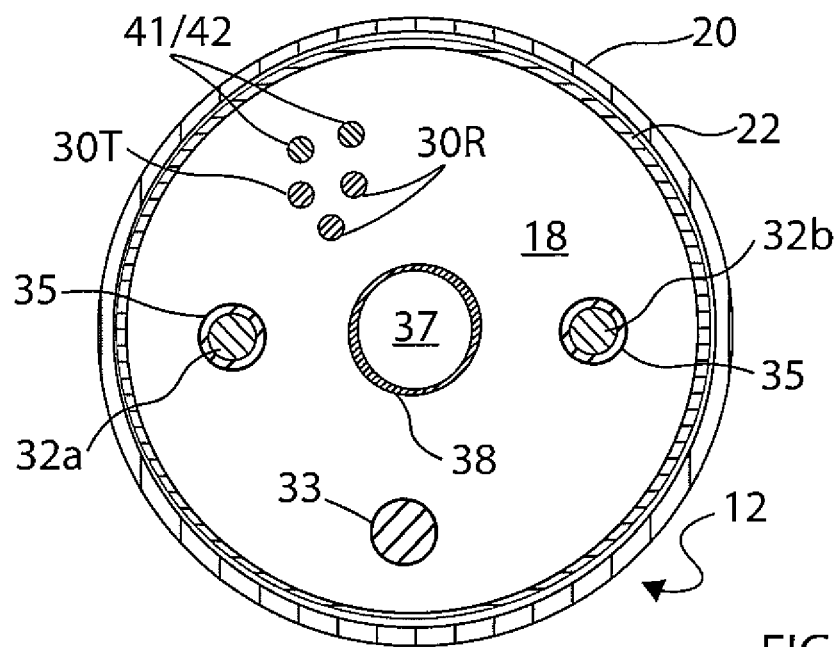
FIG. 2 is an end cross-sectional view of a catheter body of the catheter of FIG. 1, taken along line A-A.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate puller members (e.g., puller wires), lead wires, and any other desired wires, cables or tubings. If desired, the inner surface of the outer wall 20 is lined with a stiffening tube 22 to provide improved torsional stability. A disclosed embodiment, the catheter has an outer wall 20 with an outer diameter of from about 0.090 inch to about 0.94 inch and an inner diameter of from about 0.061 inch to about 0.065 inch.

Components that extend between the control handle 16 and the deflectable section 14 pass through the central lumen 18 of the catheter body 12. These components include lead wires 30T and 30R (for the tip electrode 17 and a plurality of ring electrodes 21 proximal of the tip electrode), an irrigation tubing 38 with lumen 37 for delivering fluid to the tip electrode, a cable 33 for a position sensor 34 carried in or near the distal section 15, puller wires 32a, 32b for deflecting the intermediate section 14, and a pair of thermocouple wires 41, 42 to sense temperature at the distal section 15. It is understood that in some embodiments one of the wires 41 and 42 is configured as a lead wire for delivering electrical energy to the tip electrode 17 in lieu of the lead wire 30T.

Figure 3:
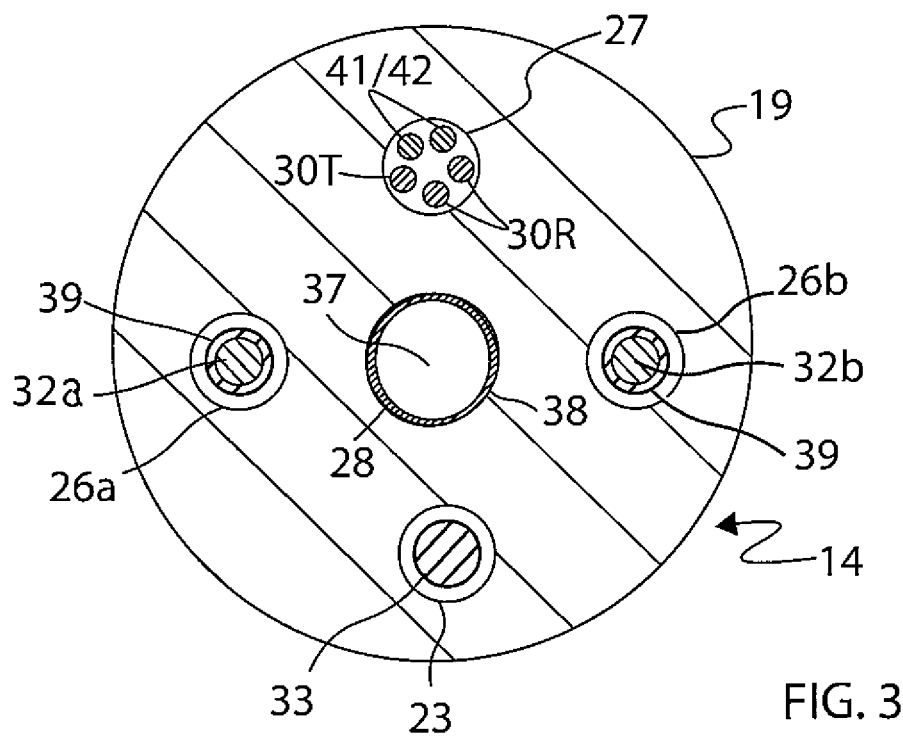
FIG. 3 is an end cross-sectional view of an intermediate section of the catheter of FIG. 1, taken along line B-B.

Illustrated in FIG. 3 is an embodiment of the intermediate section 14 which comprises a short section of tubing 19. The tubing also has a braided mesh construction but with multiple lumens, for example off-axis lumens 23, 26a, 26b and 27 and on-axis lumen 28. The lumen 27 carries the lead wires 30T and 30R, and the thermocouple wires 41 and 42. The lumen 23 carries the position sensor cable 33. The lumen 28 carries the irrigation tubing 38. The lumen 26a carries a puller wire 32a for deflection of the intermediate section. For bi-directional deflection, the diametrically-opposing lumen 26b carries a second puller wire 32b.

The tubing 19 of the intermediate section 14 is made of a suitable non-toxic material that is more flexible than the catheter body 12. A suitable material for the tubing 19 is braided polyurethane, i.e., polyurethane with an embedded mesh of braided stainless steel or the like. The size of each lumen is not critical, but is sufficient to house the respective components extending therethrough.

Each puller wire 32a and 32b has a lubricious coating, e.g. of Teflon®. The puller wires can be made of any suitable metal, such as stainless steel or Nitinol and the Teflon coating imparts lubricity to the puller wire. The puller wire preferably has a diameter ranging from about 0.006 to about 0.010 inch.

As shown in FIG. 3, the portion of each puller wire in the catheter body 12 passes through a compression coil 35 in surrounding relation to its puller wire. Each compression coil 35 extends from the proximal end of the catheter body 12 to at or near the proximal end of the intermediate section 14. The compression coils are made of any suitable metal, preferably stainless steel, and are tightly wound on themselves to provide flexibility, i.e., bending, but to resist compression. The inner diameter of the compression coil is preferably slightly larger than the diameter of the puller wire. Each portion of the puller wires distal of the compression coil 35 may extend through a respective protective sheath 39 to prevent the puller wire from cutting into the tubing 19 of the intermediate section 14 during deflection.

Proximal ends of the puller wires 32a and 32b are anchored in the control handle 16. Distal ends of the puller wires 32a and 32b are anchored in the distal section 15, as described further below. Separate and independent longitudinal movements of the puller wires relative to the catheter body 12, which results in, respectively, deflection of the intermediate section 14 along a plane, are accomplished by suitable manipulation of a deflection member of the control handle 16. Suitable deflection members and/or deflection assemblies are described in co-pending U.S. Publication No. US2010/0168827 A1, published Jul. 1, 2010, entitled DEFLECTABLE SHEATH INTRODUCER, and U.S. Publication No. US2008/0255540 A1, published Oct. 16, 2008, entitled STEERING MECHANISM FOR BI-DIRECTIONAL CATHETER, the entire disclosures of both of which are hereby incorporated by reference.

Figure 4:
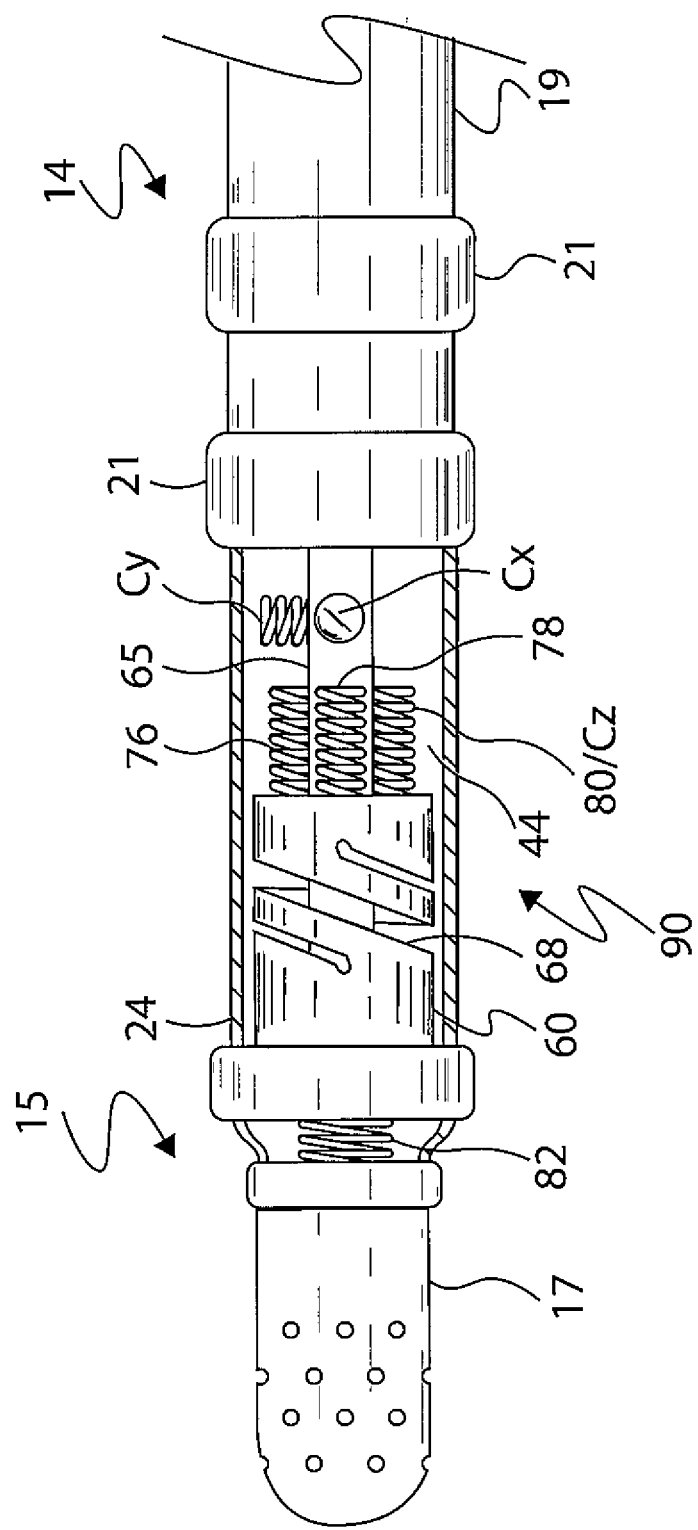
FIG. 4 is side elevational view of a distal tip section of the catheter of FIG. 1.

With reference to FIG. 4, at the distal end of the intermediate section 14 is the distal tip section 15 that includes the tip electrode 17 and a relatively short piece of non-conductive connector tubing or covering 24 between the tip electrode 17 and the intermediate section 14. In the illustrated embodiment, the connector tubing 24 has a single lumen 44 which receives a distal end of the position sensor cable 33 and allows passage of components including electrode lead wires 30T and 30R, thermocouple wires 41 and 42, and the irrigation tubing 38 into the distal section 15 and tip electrode 17. The single lumen 44 of the connector tubing 24 allows these components to reorient themselves as needed from their respective lumens in the intermediate section 14 toward their location within the distal section 15 and tip electrode 17. In the disclosed embodiment, the tubing 24 is a protective tubing, e.g., PEEK tubing, having a length ranging between 6 mm and 12 mm, more preferably about 11 mm.

The connector tubing 24 also houses a force sensor 90. Aspects of a force sensor similar to force sensor are described in U.S. Pat. No. 8,357,152, issued on Jan. 22, 2013 to Govari et al., entitled CATHETER WITH PRESSURE SENSING, and in U.S. Patent Publication No. 2011/0130648, to Beeckler et al., filed Nov. 30, 2009, entitled CATHETER WITH PRESSURE MEASURING TIP, both of whose disclosures are incorporated herein by reference.

Figure 5:
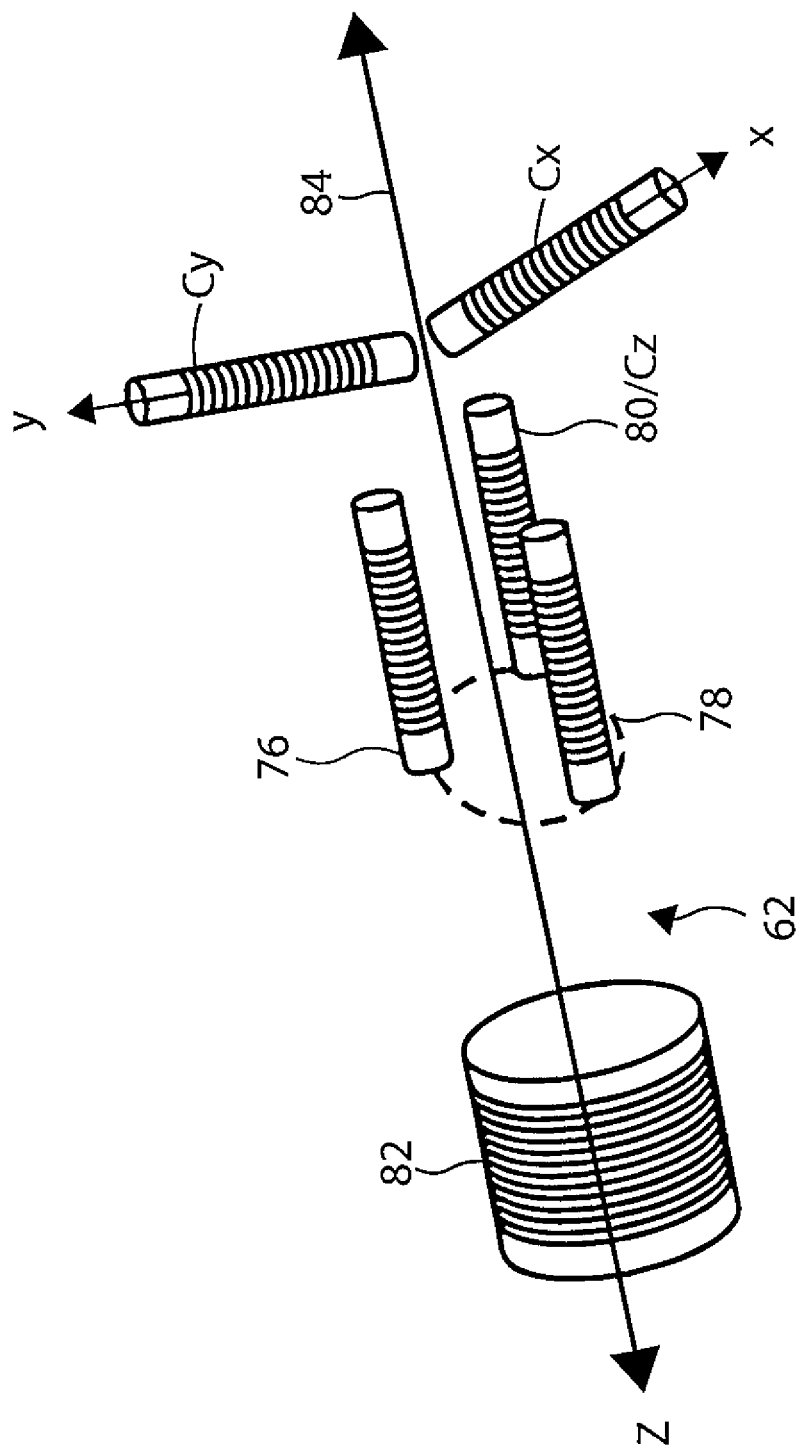
FIG. 5 is a perspective illustration representative of various coils in the distal tip section of FIG. 4.

With reference to FIG. 4 and FIG. 5, the force sensor 90 includes a resilient coupling member 60, which forms a spring joint. In some embodiments, the coupling member 60 has hollow tubular form with a central lumen 68 therethrough. Coupling member 60 typically has one or more helices cut or otherwise formed in the member, so that the member behaves as a spring. In some embodiments, the coupling member 60 is formed of a superelastic alloy, such as nickel titanium (Nitinol), within force sensor 90.

The force sensor 90 includes a joint sensing assembly comprising coils 76, 78, 80 and 82 that provides accurate reading of any dimensional change in axial displacement and angular deflection in the spring joint, including when the tip electrode 17 is angularly displaced from a longitudinal axis 84 of the catheter, such as then the tip electrode comes into contact with tissue. These coils are one type of magnetic transducer that may be used with the catheter. A "magnetic transducer," in the context of the present patent application and in the claims, means a device that generates a magnetic field in response to an applied electrical current and/or outputs an electrical signal in response to an applied magnetic field. Although the embodiments described herein use coils as magnetic transducers, other types of magnetic transducers may be used in alternative embodiments, as will be apparent to those skilled in the art.

The coils in the sensing assembly are divided between two subassemblies on opposite sides of the spring joint. One subassembly comprises coil 82 distal of the spring joint, which is driven by a current, via a wire (included in the cable 33), to generate a magnetic field. This field is received by a second subassembly, comprising coils 76, 78 and 80, which are located proximal of the spring joint, in a section of the connector tubing 24 that is spaced axially apart from and proximal of the coil 82. The term "axial," as used in the context of the present patent application and in the claims, refers to a direction along or parallel to the longitudinal axis 84 of the catheter. The coil 82 typically lies on-axis with the longitudinal axis 84.

Coils 76, 78 and 80 are fixed in connector tubing 24 at the same proximal distance from the coil 82 but at different radial locations. (The term "radial" refers to coordinates about the longitudinal axis 84.) Specifically, in the illustrated embodiment, the coils 76, 78 and 80 are all located in the same plane perpendicular to the longitudinal axis 84 but at different equi-azimuthal angles about the longitudinal axis 84, that is, the three coils are spaced azimuthally 120 degrees apart at the same axial distance from the coil 82 along the longitudinal axis 84.

The coils 76, 78 and 80 generate electrical signals in response to the magnetic field transmitted by coil 82. These signals are conveyed by wires (part of the cable 33) extending proximally from the distal section 15, through the lumen 23 of the intermediate section 14, through the lumen 18 of the catheter body 12 and into the control handle 16. The signals are processed by a remote processor in order, for example, to measure the axial displacement of spring joint along the longitudinal axis 84, as well as to measure the angular deflection of the joint from the longitudinal axis 84. From the measured displacement and deflection, the processor is able to evaluate, typically using a previously determined calibration table, a magnitude and a direction of the force on the spring joint.

The same processor (or another processor) detects and measures the location and orientation of distal section 15. The method of measurement may be by any convenient process known in the art. In one embodiment, magnetic fields generated external to a patient create electric signals in elements in the distal section 15, and the processor uses the electric signal levels to determine the distal section location and orientation. Alternatively, the magnetic fields may be generated in the distal section 15, and the electrical signals created by the fields may be measured external to patient. As shown in FIG. 4 and FIG. 5, the elements in distal section 12 that are used to position and locate the distal section) 12 include orthogonal coil $C_x$ aligned with the X axis, orthogonal coil $C_y$ aligned with the Y axis, and one of the coil 76, 78 and 80 (in addition to their use as elements of force sensor), for example, the coil 80 aligned with the Z axis as orthogonal coil $C_z$. The coils $C_x$, $C_y$, $C_z$/80 are housed in the connector tubing 24, within the lumen 68 of the coupling member 60. These coils are the sensing components of the electromagnetic position sensor 34 to which the cable 33 is connected. In some embodiments, the catheter includes a single axial sensor (SAS) cable assembly in lieu of the cable 33 and the electromagnetic position sensor 34 for position and location sensing. A SAS cable assembly suitable for use is described in U.S. Pat. No. 8,792,962, titled CATHETER WITH SINGLE AXIAL SENSORS, the entire disclosure of which is incorporated herein by reference.

Figure 6:
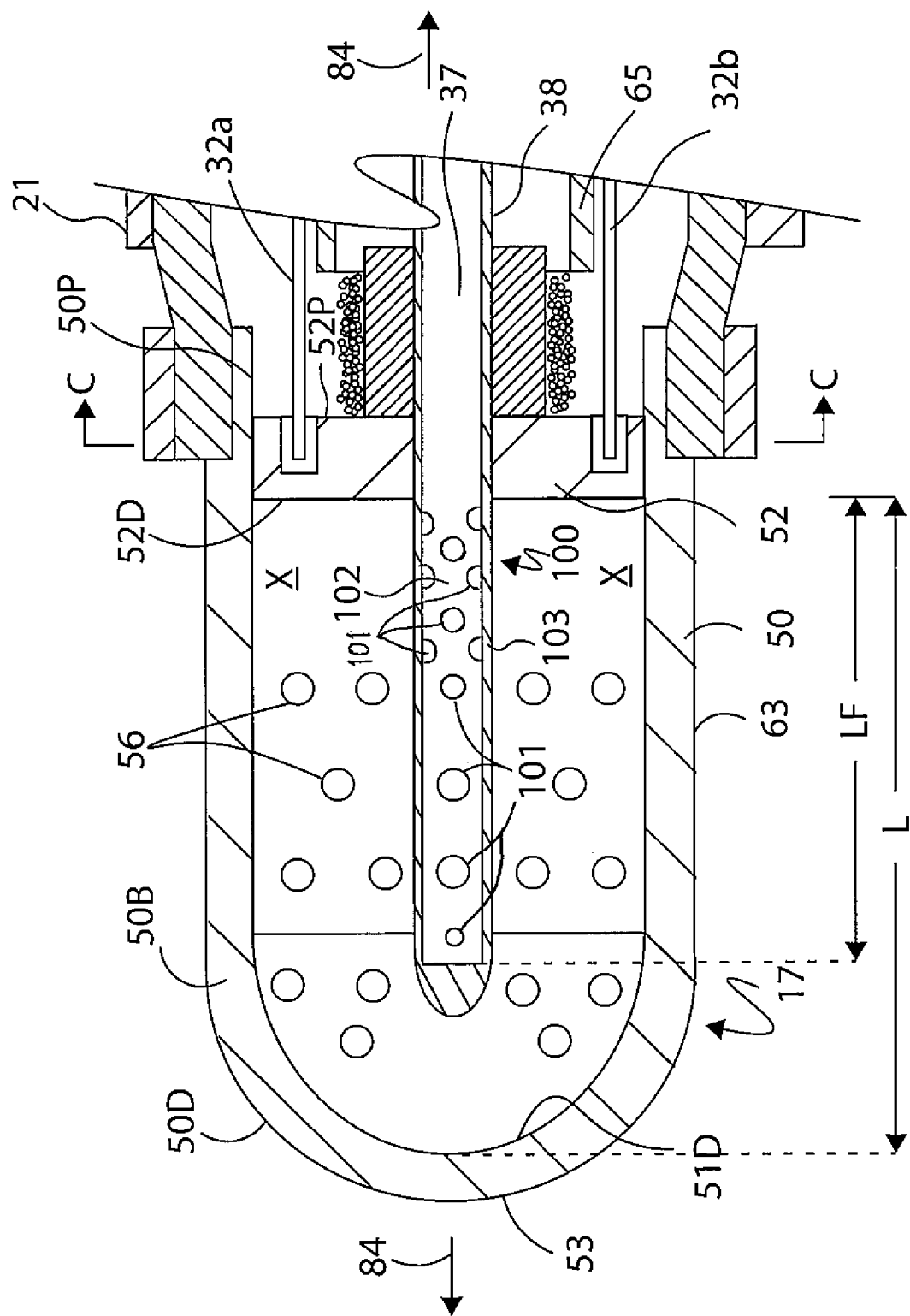
FIG. 6 is a side-cross-sectional view of the tip electrode of FIG. 4.

With reference to FIG. 6, the irrigated tip electrode 17 has a two-piece construction that includes an electrically-conductive dome shell 50 and an electrically-conductive internal support member or "plug" 52 which jointly define a cavity of an internal plenum chamber 51 that is surrounded, enclosed and sealed by the shell 50 and the support member 52. The chamber has a longitudinal length L extending between a distal face 52D of the plug 52 and a distal inner wall 51D. The shell 50 has a hollow cylindrical body 50B with an open proximal portion 50P and a closed distal portion 50D adapted for tissue contact. The distal portion 50D has a dome atraumatic distal end 53. Formed in shell wall 63 are a plurality of fluid exit ports 56 that allow fluid communication between the chamber 51 and outside the shell 50.

The shell 50 and the plug 52 are constructed of a biocompatible metal, including a biocompatible metal alloy. A suitable biocompatible metal alloy includes an alloy selected from stainless steel alloys, noble metal alloys and/or combinations thereof. In one embodiment, the shell is constructed of an alloy comprising about 80% palladium and about 20% platinum by weight. In an alternate embodiment, the shell 50 and the member 52 are constructed of an alloy comprising about 90% platinum and about 10% iridium by weight. In some embodiments, the shell is formed by deep-drawing manufacturing process which produces a sufficiently thin but sturdy shell wall that is suitable for handling, transport through the patient's body, and tissue contact during mapping and ablation procedures.

The lead/thermocouple wires 30T, 41 and/or 42 and the irrigation tubing 31 pass proximally from the tip electrode 17 through a protective, nonconductive tubing 65 (FIG. 4). The wires and the irrigation tubing pass further through the lumens 27 and 28 of the tubing 19 of the intermediate section 14 and through the lumen 18 of the catheter body 12. The shell 50 and the plug 52 facilitate the provision of a plenum condition within the chamber 51; that is, where fluid is forced or delivered in the chamber 51 and then passes through the exit ports 56 formed in shell wall 63 to exit the tip electrode 17.

Figure 7:
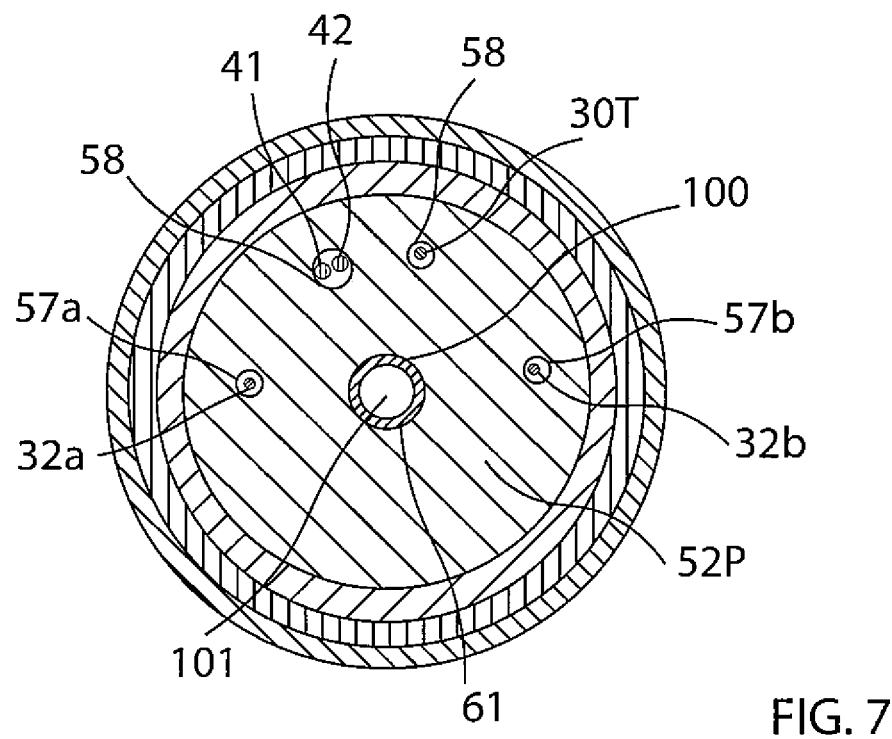
FIG. 7 is an end cross-sectional view of the tip electrode of FIG. 5.

As shown in FIG. 7, the plug 52 has a plurality of holes. In the illustrated embodiment, the plug 52 has four blind holes, namely, 57a, 57b and 58, on its proximal face 52P and one through-hole 61. The blind holes 57a and 57b are off-axis, diametrically opposed and generally in longitudinal alignment with lumens 26a and 26b of the deflectable section 14 for receiving and anchoring the puller wire 32a and 32b, respectively. One or more blind hole(s) 58 are off-axis and adapted to receive and anchor distal ends of lead wire 30T and thermocouple wires 41 and 42. As mentioned, in some embodiments, one of the thermocouple wires 41 and 42 is configured as a lead wire for the tip electrode 17, obviating the need for the separate lead wire 30T. The through-hole 61 is on-axis and adapted to receive a distal portion of the irrigation tubing 38.

Figure 8:
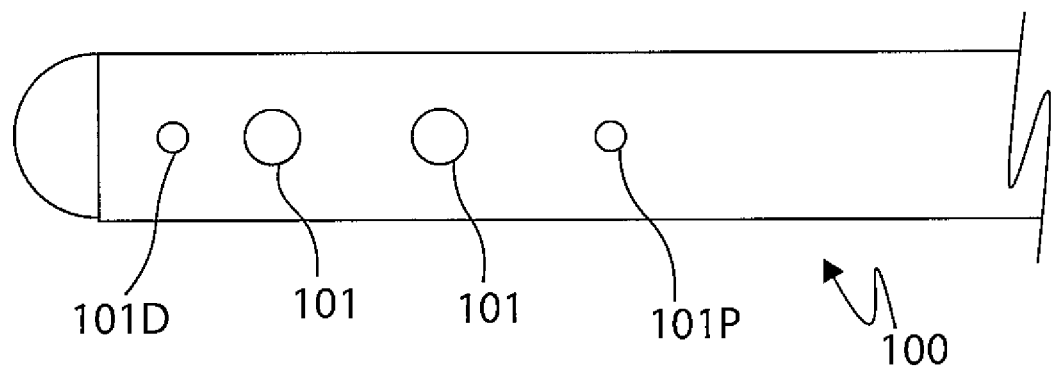
FIG. 8 is a side-elevational view of a fluid distribution tube, in accordance with an embodiment of the present invention.
Figure 9:
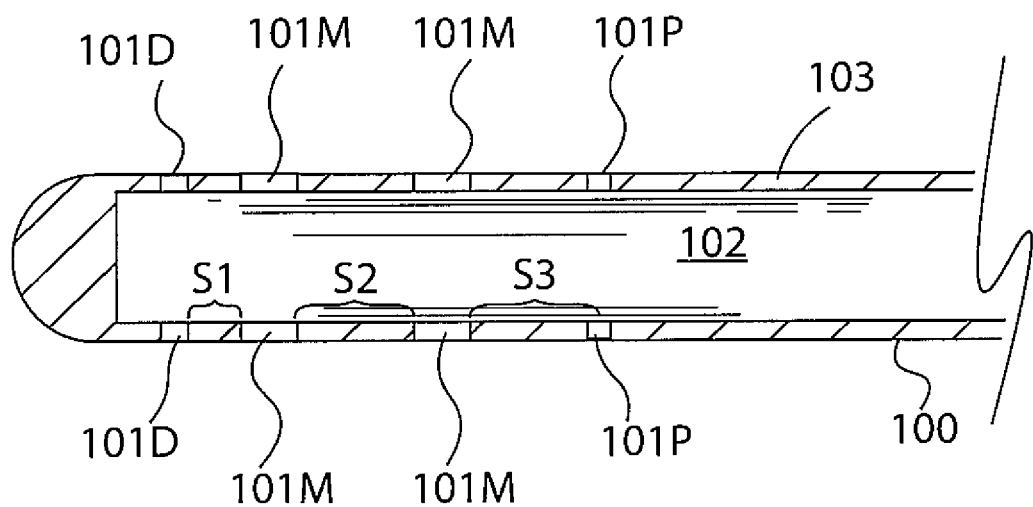
FIG. 9 is a side cross-sectional view of the fluid distribution tube of FIG. 8.
Figure 10:
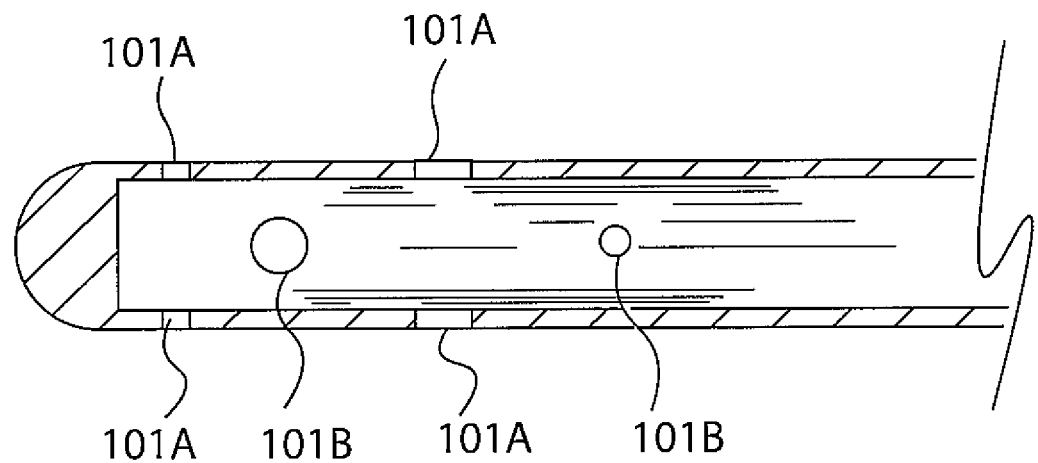
FIG. 10 is a side cross-sectional view of a fluid distribution tube, in accordance with another embodiment of the present invention.

As shown in FIG. 6, extending through the through-hole 61 from a distal face 52D of the plug 52 is an elongated hollow fluid distribution tube 100 formed with a plurality of graduated fluid distribution apertures 101 arranged in a predetermined pattern. The fluid tube 100 extends linearly and distally into the chamber 51, on-axis with the longitudinal axis 84 of the catheter. The fluid tube 100 has a closed distal end. Center lumen 102 of the fluid tube 100 is in communication with the lumen 37 of the irrigation tubing 38 and also with the fluid apertures 101 formed in side wall 103 of the fluid tube 100. Advantageously, the lumen 102 of the fluid tube 101 in the chamber 51 reaches deep into the chamber by extending distally toward the distal end 51D of the chamber 51 and having a length LF ranging between about 0.5 and 1.0, more preferably about 0.6 and 0.8, of the length L of the chamber 51, where the side wall 103 of the fluid tube 101 is configured with the fluid apertures 101 in a predetermined pattern. The pattern includes, for example, fluid apertures 101 spanning along the length of the fluid tube 100, so that there is at least one proximal aperture 101P and at least one distal aperture 101D, each occupying a different longitudinal position in the fluid tube 100, as show in FIG. 8. Moreover, the size and/or shape of each aperture 101 may vary. In the embodiment of FIG. 9, the fluid tube 100 includes eight apertures: four pairs of diametrically-opposed apertures, with two smaller-sized, most-distal apertures 101D, two smaller-sized, most-proximal apertures 101P, and two larger-sized, mid-apertures therebetween 101M. The spacing S1 and S2 and S3 between adjacent apertures differs, for example, where a more-distal spacing is lesser than a more-proximal spacing, or where S1<S2<S3. In some embodiments, the fluid apertures 101 are longitudinally aligned, occupying similar radial positions in the side wall 103, as shown in FIG. 8 and FIG. 9. In some embodiments, longitudinally-adjacent apertures 101 occupy different radial positions in the side wall 103, for example, apertures 101A are 90 degrees radially offset from apertures 101B, as shown in FIG. 10.

In some embodiments, at least some of the apertures 101 are sized smaller than the ports 56 of the shell 50. In some embodiments, at least some of the apertures 101 are sized about the same as the ports 56. In some embodiments, at least some of the apertures 101 are sized larger than the ports 56. In some embodiments, at least one of the apertures 101 is more proximal than the most proximal port(s) 56.

The configurations of the apertures 101 spanning along the length of the fluid tube 100 advantageously provide predetermined distribution patterns of irrigation fluid to both the proximal and distal portions of the chamber 51 which provide better cooling of the tip electrode 17 regardless of the configuration of the exit ports 56 in the wall 63 of the shell 50. Thus, in the portion(s) of the shell 50 are lacking or devoid of exit ports 56, e.g., the proximal portion of the shell 50 near the plug 52 (see "x" in FIG. 6), the fluid tube 100 and its apertures 101 enable improved circulation of cooling fluid within the chamber 51, in contrast to prior plenum chamber where irrigation fluid enters the chamber 51 merely at its proximal end without other mechanisms or forces that delivers fluid more uniformly throughout the entirety of the chamber. The different sizing and/or shape of the apertures 101 enable the fluid to enter the chamber 51 at different velocities for improving circulation within the chamber 51. Improved circulation improves cooling of all portions of the tip electrode 17 and thus decrease the risk of char formation on all portions of the tip electrode, especially the proximal portion of the tip electrode and portions lacking or devoid of exit ports. By applying computation fluid dynamics (CFD) to variations in tip electrode parameters, including, for example, dome shell/chamber size, the plurality, location, shape and/or size of exit ports 56 in the shell 50, the relative length of the fluid tube 100 to the chamber length, the plurality location, shape and/or size of apertures 101, fluid dynamics within the tip electrode 17 are calculated and readily adjusted, as desired or appropriate.

It is understood that the fluid tube 100 may be constructed as a portion of the irrigation tubing 38, for example, of a similar material, as a proximal portion of the irrigation tubing. Alternatively, the fluid tube 100 may be constructed of a different material and/or as a separate or different component from the irrigation tubing, with fluid communication enabled by the through-hole 60 in the plug 52, or by another fluid tubing. In any case, the fluid tube 100 is constructed for fluid communication between its lumen 102 and the lumen 37 of the irrigation tubing 38, either directly or indirectly, such that fluid is passed and delivered between the irrigation tubing 38 and the fluid tube 100.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Notably, the drawings are not necessarily to scale, and any one or more features of an embodiment may be included in any other embodiment in addition to or in lieu of any feature, as desired or appropriate. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrophysiologic catheter having:
   an elongated catheter body;
   a control handle proximal of the elongated catheter body; and
   a tip electrode distal of the elongated catheter body, the tip electrode configured for irrigation and comprising:
      a shell comprising a generally cylindrical proximal body, and a distal end configured to contact tissue, the shell comprising an internal cavity and a plurality of radially spaced apart generally circular side ports in the generally cylindrical proximal body and one or more end ports in the distal end, each of the plurality of generally circular side ports and the one or more end ports extending from the internal cavity through a shell wall to outside the shell;
      a support member, the shell and the support member defining the internal cavity, a proximal shell portion of the shell that is distal of a distal end of the support member being devoid of any side ports; and
      a fluid distribution tube extending through the support member longitudinally into the internal cavity, the fluid distribution tube having a side wall with a plurality of apertures in fluid communication with the internal cavity, at least one of the plurality of apertures of the fluid distribution tube being more proximal than a most-proximal one of the plurality of generally circular side ports of the shell such that the at least one of the plurality of apertures that is more proximal than the most-proximal one of the plurality of generally circular side ports of the shell is in fluid communication with the proximal shell portion that is devoid of any side ports, and at least one other of the plurality of apertures of the fluid distribution tube being distal of the most-proximal one of the plurality of generally circular side ports of the shell, the at least one of the plurality of apertures that is more proximal than the most-proximal one of the plurality of generally circular side ports of the shell having a smaller size than at least one other of the plurality of apertures that is distal of the at least one of the plurality of apertures that is more proximal than the most-proximal one of the plurality of generally circular side ports of the shell.

2. The catheter of claim 1, wherein the plurality of apertures of the fluid distribution tube are arranged in a predetermined pattern.

3. The catheter of claim 2, wherein the predetermined pattern includes longitudinal alignment of the plurality of apertures.

4. The catheter of claim 2, wherein the predetermined pattern includes a greater spacing between more-proximal adjacent apertures and a lesser spacing between more-distal adjacent apertures.

5. The catheter of claim 2, wherein the predetermined pattern includes the plurality of apertures having different radial positions in the side wall of the fluid distribution tube.

6. The catheter of claim 2, wherein the predetermined pattern of the plurality of apertures of the fluid distribution tube comprises:
one first pair of proximal apertures that are diametrically opposed and longitudinally aligned,
two second pairs of middle apertures, each of the middle apertures of each of the two pairs of middle apertures being diametrically opposed and longitudinally aligned, and
one third pair of distal apertures that are diametrically opposed and longitudinally aligned,
the first pair of proximal apertures being proximal of the second pairs of middle apertures, and the second pairs of middle apertures being proximal of the third pair of distal apertures,
a first spacing between the first pair of proximal apertures and proximal-most pair of the two pairs of middle apertures being greater than a second spacing between the two pairs of middle apertures, and the second spacing between the two pairs of middle apertures being greater than a third spacing between the third pair of distal apertures and a distal-most pair of the two pairs of middle apertures.

7. The catheter of claim 1, wherein the plurality of apertures of the fluid distribution tube have different sizes.

8. The catheter of claim 1, wherein the plurality of apertures of the fluid distribution tube have different shapes.

9. The catheter of claim 1, further comprising an irrigation tubing in fluid communication with the fluid distribution tube.

10. The catheter of claim 1, wherein the internal cavity has a first length and the fluid distribution tube extends into the internal cavity by a second length that ranges between 50% and 100% of the first length.

11. The catheter of claim 1, wherein the internal cavity has a first length and the fluid distribution tube extends into the internal cavity by a second length that ranges between 60% and 80% of the first length.

12. An electrophysiologic catheter having:
an elongated catheter body;
a control handle proximal of the elongated catheter body; and
a tip electrode distal of the elongated catheter body, the tip electrode configured for irrigation and comprising:
a shell comprising an internal cavity and comprising a generally cylindrical proximal body, a distal end configured to contact tissue, a plurality of radially spaced apart generally circular side ports in the generally cylindrical proximal body, and one or more end ports in the distal end, each of the plurality of generally circular side ports and the one or more end ports extending from the internal cavity through a shell wall to outside the shell;
a support member, the shell and the support member defining the internal cavity, a proximal shell portion of the shell that is distal of a distal end of the support member being devoid of any side ports; and
a fluid distribution tube extending through the support member longitudinally into the internal cavity, the fluid distribution tube having a side wall with a plurality of apertures in fluid communication with the internal cavity, one or more of the plurality of apertures having a size different than one or more of either the one or more end ports or the plurality of generally circular side ports of the shell, and at least one of the plurality of apertures of the fluid distribution tube being more proximal than a most-proximal one of the plurality of generally circular side ports of the shell such that the at least one of the plurality of apertures that is more proximal than the most-proximal one of the plurality of generally circular side ports of the shell is in fluid communication with the proximal shell portion that is devoid of any side ports, and at least one other of the plurality of apertures of the fluid distribution tube being distal of the most-proximal one of the plurality of generally circular side ports of the shell, the one or more of the plurality of apertures that is more proximal than the most-proximal one of the plurality of generally circular side ports of the shell having a smaller size than at least one other of the plurality of apertures that is distal of the one or more of the plurality of apertures that is more proximal than the most-proximal one of the plurality of generally circular side ports of the shell.

13. The catheter of claim 12, wherein the internal cavity has a first length and the fluid distribution tube extends into the internal cavity by a second length that ranges between 50% and 100% of the first length.

14. The catheter of claim 12, wherein the plurality of apertures of the fluid distribution tube are arranged in a predetermined pattern.

15. The catheter of claim 14, wherein the predetermined pattern includes longitudinal alignment of the plurality of apertures.

16. The catheter of claim 14, wherein the predetermined pattern includes a greater spacing between more-proximal adjacent apertures and a lesser spacing between more-distal adjacent apertures.

17. The catheter of claim 14, wherein the predetermined pattern includes the plurality of apertures having different radial positions in the side wall of the fluid distribution tube.

18. The catheter of claim 12, wherein the plurality of apertures of the fluid distribution tube have different sizes.

19. The catheter of claim 12, wherein the plurality of apertures of the fluid distribution tube have different shapes.

20. The catheter of claim 12, further comprising an irrigation tubing in fluid communication with the fluid distribution tube.

* * * * *